United States Patent [19]
Millner

[11] Patent Number: 5,435,033
[45] Date of Patent: Jul. 25, 1995

[54] INTERDENTAL TOOTHCLEANER HOLDER

[76] Inventor: Don E. Millner, 212 Bruce Rd., Washington Crossing, Pa. 18977

[21] Appl. No.: 276,601

[22] Filed: Jul. 18, 1994

[51] Int. Cl.$^6$ .................... A61C 17/20; A61C 17/22; A46B 9/04
[52] U.S. Cl. ........................... 15/22.1; 15/145; 15/167.1; 15/176.5; 15/176.6; 15/206; 132/321
[58] Field of Search ............... 15/145, 146, 167.1, 15/176.1–176.6, 194, 202, 206, 22.1; 132/321; 433/147

[56] References Cited

U.S. PATENT DOCUMENTS

| | | | |
|---|---|---|---|
| 3,204,275 | 9/1965 | Baker | 15/172 |
| 3,559,226 | 2/1971 | Burns | 15/167.1 |
| 4,030,199 | 6/1977 | Russell | 15/106 |
| 4,222,143 | 9/1980 | Tarrson et al. | 15/105 |
| 4,387,479 | 6/1983 | Kigyos | 15/167.1 |
| 4,395,943 | 8/1983 | Brendii | 15/167.1 |
| 4,710,996 | 12/1987 | Tarrson et al. | 15/105 |
| 4,805,252 | 2/1989 | Tarrson et al. | 15/167.1 |
| 5,027,467 | 7/1991 | Tarrson et al. | 15/176.5 |
| 5,029,358 | 7/1991 | Zimmerman | 15/167.1 |
| 5,123,841 | 6/1992 | Millner | 433/125 |
| 5,201,091 | 4/1993 | Tarrson et al. | 15/167.1 |
| 5,311,632 | 5/1994 | Center | 15/22.1 |
| 5,313,684 | 5/1994 | Fitjer | 15/167.1 |
| 5,331,708 | 7/1994 | Ponzini | 15/167.1 |

Primary Examiner—Mark Spisich
Attorney, Agent, or Firm—Donald S. Cohen

[57] ABSTRACT

A holder for an interdental toothcleaner of the type having a substantially rigid but flexible stem and cleaning means on the stem. The holder includes a neck having a tip projection radially therefrom adjacent one end thereof and a slot extending longitudinally therealong from the one end and diametrically opposite the tip. A hole extends through the tip and transversely across the neck to the slot. A cap having a passage therethrough which is open at one end and closed at the other end is on the neck and slidable therealong. The cap has a first slot therethrough which extends from its open end and in which the tip slides. The cap has a second slot therethrough diametrically opposite the first slot. The second slot is closed at both ends with the ends being spaced from the ends of the cap. The stem of a toothcleaner passes through the hole in the tip and projects beyond the groove in the neck and through the second slot in the cap. The cap is moved on the neck causing one end of the second slot to engage the stem and bend it into the groove in the neck. The cap holds the stem in the groove to secure the toothcleaner to the support.

17 Claims, 3 Drawing Sheets

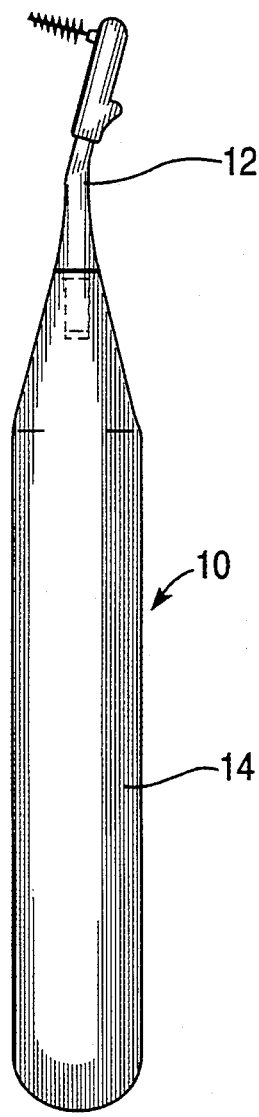
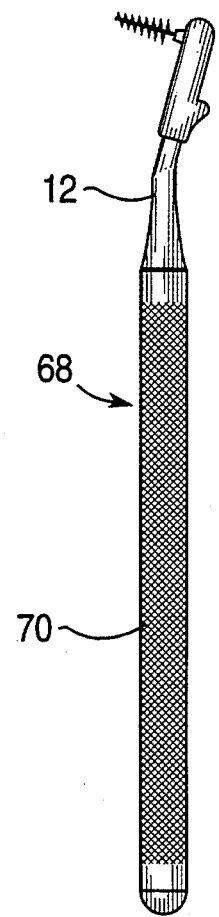
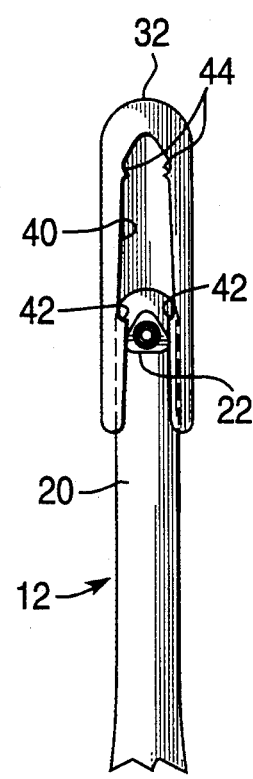
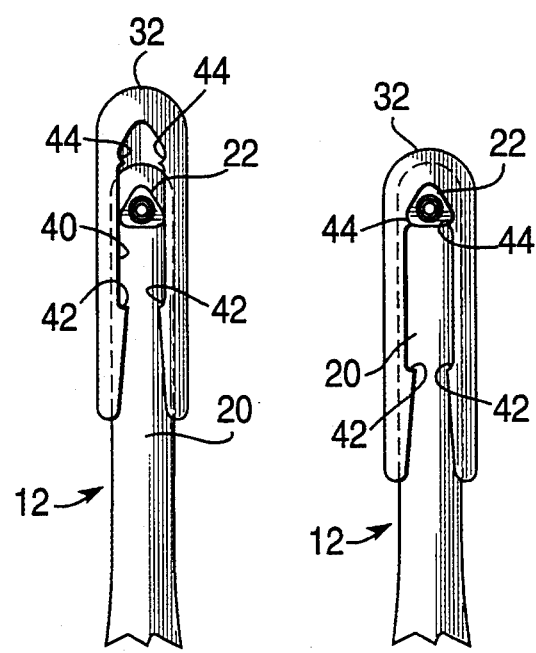
FIG. 1    FIG. 12
FIG. 2    FIG. 3    FIG. 4

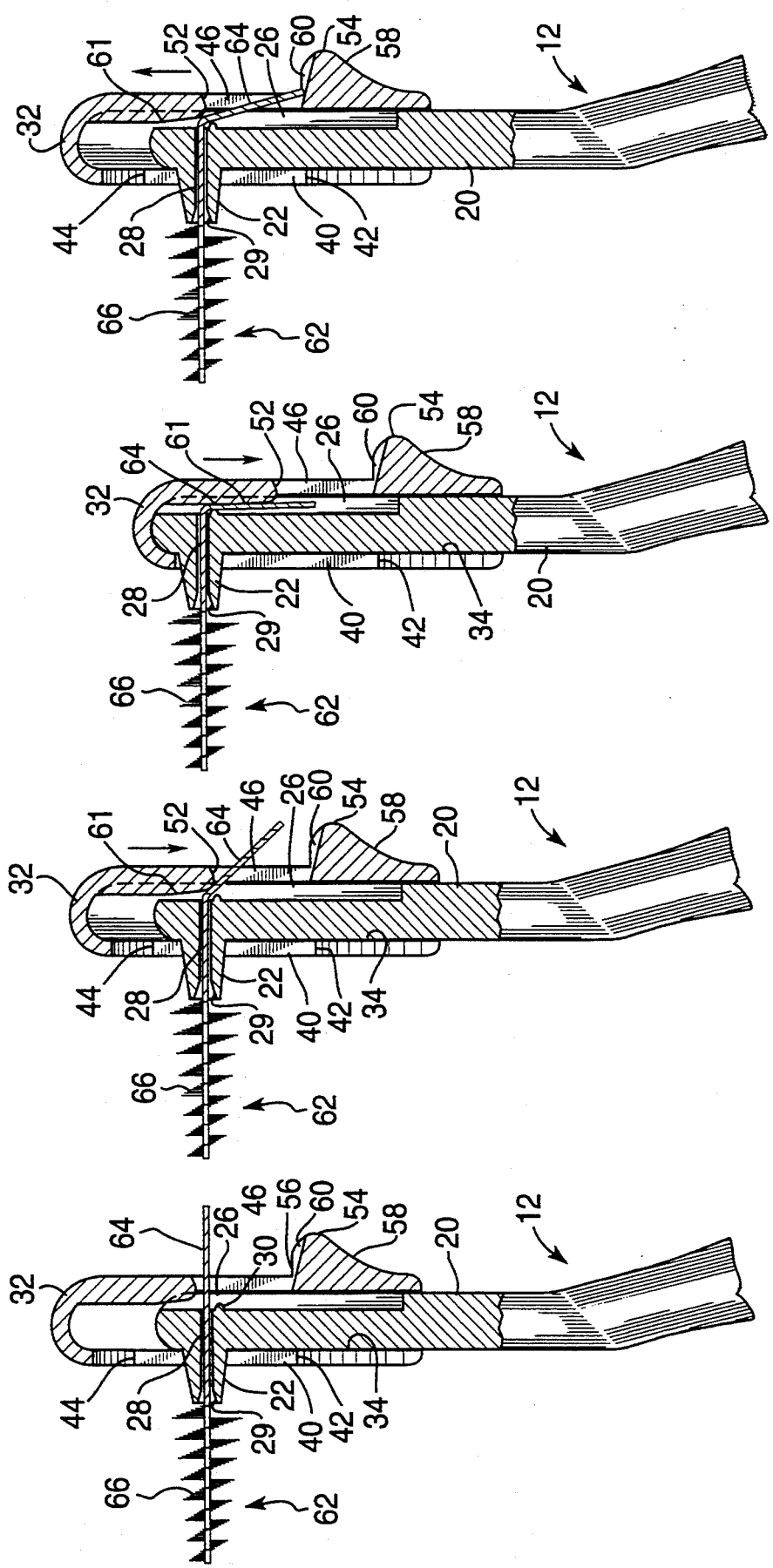

INTERDENTAL TOOTHCLEANER HOLDER

FIELD OF THE INVENTION

The present invention is directed to an interdental toothcleaner holder, and, more particularly, to an interdental toothcleaner holder which holds the toothcleaner tightly but allows for ease of removal and replacement of worn toothcleaners.

BACKGROUND OF THE INVENTION

The toothcleaner most widely used for personal oral hygiene is a toothbrush which usually consists of parallel rows of tufted bristles brushing components. When used, as professionally recommended, at a 45 degree angle to the gum tooth interface and applied with a slight vibrating motion, these conventional toothbrushes are able to efficiently remove plaque only from freely accessible, easily visible cheek side, tongue side and chewing surfaces of the tooth.

Regardless of the many claims of enhanced efficacy, all conventional toothbrushes, including electric toothbrushes, function in the same manner and are inherently inefficient. Their actions, redundant to the natural cleaning mechanism of the mouth, rarely clean better than the abrasiveness of food, salivary dilution, and/or the normal rubbing functions of the tongue, cheek and lips.

Conventional toothbrushes all share a major fault. They tend to hop, skip, jump, and buff over the recessed, hidden areas between the teeth. By doing so, they almost completely miss the sites which harbor the greatest concentration of pathogenic bacterial plaque, the interdental col. When compared with the use of floss or an interdental brush, the plaque removing capabilities of a conventional toothbrush are woefully inadequate.

Currently, flossing is recommended as the most efficient means to clean a healthy, never-diseased mouth. Sadly, few adults floss on a daily basis. Inconvenient, unproductive and difficult to master, the flossing habit is rarely established before the disease process is firmly entrenched. Unfortunately, for those three out of four adults who acquire gum disease, flossing may come too late.

When interdental plaque is not removed by daily flossing or interdental brushing, the body's immune system identifies it as a foreign irritant and tries to destroy it. Since plaque continues to build up after every meal, the body can never completely defend itself. Over a period of weeks, the immune system becomes worn down by the chronic infection. In a last ditch effort, the body produces powerful plaque killing toxins. Unfortunately, the toxins are so powerful that they bore into the gums and supporting bone socket to create a crater like periodontal pocket.

The resultant pocket is less accessible to traditional oral home care. Floss gets "hung up" on the swollen, inflamed gums that occur at the upper edges of the pocket. Floss also tends to span over the invaginated root surfaces that are exposed in the infected interdental col. Without a means of thorough daily cleaning of the pocket, the disease process becomes self perpetuating. Eventually, most of the thick supporting socket is destroyed between the teeth.

Although the conventionally brushed gum tissue and the bone support on the cheek side and the tongue side of the tooth continue to appear healthy, they are but a paper thin facade. Lacking the supporting bone between the teeth, those seemingly firm areas are subject to ruination from just the slightest forces of mastication. Tragically, with its socket gone, a tooth simply falls out of the mouth.

Interdental/interproximal toothbrushes are now recognized as probably the most effective means to address interdental plaque in the mouths of persons with prosthetics, orthodontics and/or periodontal problems. This type of toothbrush is shown in U.S. Pat. No. 3,559,226 to R. L. Burns, issued Feb. 2, 1971, entitled "Tooth Brush For Interproximal Areas", U.S. Pat. No 4,222,143, to E. B. Tarrson et al., issued Sep. 16,1980, entitled "Interproximal Brush Handle", U.S. Pat. No 4,395,943, to P. Brandli, issued Aug. 2, 1983, entitled "Interproximal Toothbrush". Such toothbrushes are generally made of a pair of thin twisted wires with nylon like bristles of variable stiffness, captured by the wires and extending radially from the wires. In some of these toothbrushes the bristles are of various lengths, in the form of a cone, with the tip of the cone having the shortest bristles being at the end of the twisted wires. These interdental toothbrushes are small, about the diameter of a pipe cleaner, are disposable, and are often used in conjunction with a toothbrush handle.

Interdental toothbrushes, by virtue of the fact that they ARE a "toothbrush", are familiar and rapidly assimilated by the average user. Easy to master and visibly more productive than floss, they can navigate deep into the interdental col and its hidden invaginated root walls to bring up identifiable plaque. This feedback mechanism provides the tangible evidence that encourages the brushing habit.

Used daily, interdental brushing eliminates plaque. With the bacterial irritant missing, the exaggerated immune response subsides and the swollen tissue that surrounds the col shrinks to eliminate the periodontal "pocket". Although the contour of the col rarely regenerates to its pre-diseased morphology, it does become more open, accessible and easier to maintain.

Considering that disease elimination, along with stabilization and maintenance, are currently recognized as the ideal outcomes of periodontal therapy, interdental brushing can be considered a conservative, inexpensive, noninvasive and natural cure for gum disease.

Among other applications, the interdental toothbrush is utilized in daily personal hygiene to clean orthodontic appliances, fixed bridgework and implants. Additionally, it is ideal for the physically challenged, for whom flossing may be impossible.

Heretofore, it was recommended that the interproximal brush, as a plaque removing instrument, be pushed horizontally through an open interproximal space to remove supragingival (above the gum) plaque. I have found that when the brush tip is angled apically, 45 degrees to the long axis of the tooth, it can safely and more efficiently disrupt plaque from the deepest subgingival aspects of the interdental col. This new application has been very successful reducing or eliminating periodontal infections missed by previously taught techniques.

Additionally, a sonically resonating brush provides greater safety, efficacy, and economy than a manual action brush. Such a sonically resonating brush is shown in U.S. Pat. No. 5,123,841, to D. E. Millner, issued Jun. 23, 1992, entitled "Interproximal Dental Plaque Remover". A sonically resonating interdental brush burrows safely along the path of least resistance to the deepest part of the pocket. Without the poking action of a manual brush, fragile disposable tips bend less and last longer. Of greatest merit, a vibrating brush produces a sonic cavitation effect. Its energized bristles strike plaque off the tooth surface hundreds of times per application.

Furthermore, unlike conventional toothbrushes, interdental brushes need to be rinsed clean after each of the 28 "between the teeth" sites that potentially can be accessed during a brushing session. The hygienic removal of plaque from the brush tip, normally performed by manually rubbing it under water, is enhanced by the vibrating brush's ability to rapidly clean itself off under the tap.

Although most of the interdental brushes mentioned in the prior art are of a functional design, their handles/holders left much to be desired. To firmly secure the interdental brush tip to a handle, many of the brush designs require a severe right angle bend at the end of the twisted wire. For example, see U.S. Pat. No. 3,559,226 to R. L. Burns, issued Feb. 2, 1971, entitled "Interproximal Brush Handle", and U.S. Pat. No 4,710,996 to E. B. Tarrson et al., issued Dec. 8, 1987 entitled "Interdental Brush Handle" as showing a few such designs. Bending the wire of the brush as required in the designs of these patents makes it difficult to replace worn out brushes.

It has been found that the replacement of interdental brushes can be required as frequently as daily for inexperienced users or up to bimonthly for experienced users. Thus, it is necessary to be able to easily and quickly replace the brushes in the holder. Therefore, it would be most desirable to have a handle for an interdental brush which allows the brushes to be replaced in the handle easily and quickly.

Additionally, a number of recently developed interdental toothbrushes include hinges which must be flexed and joints which must be opened and closed many times over the lifetime of its handle in order to replace an interdental brush. Examples of such type of interdental toothbrushes are shown in U.S. Pat. No. 5,029,358 to W. Zimmerman, issued Jul. 1, 1991, entitled "Interproximal Brush", and U.S. Pat. No. 5,201,091 to E. B. Tarrson et al., issued Apr. 13, 1993 entitled "Toothbrush". It has been found that the opening and closing of these anchorages, as required in the designs of the above patents, can expose their fragile junctures to premature failure from improper use. Thus, it is necessary to have an interdental brush holder that can sustain moderate abuse from the average user. Therefore it is desirable to have a handle for an interdental brush that is strong and will not fall apart when replacing interdental brush tips.

Furthermore, a variety of interdental cleaning tips are now commonly available. Although most conform to a standardized format, some do not. Some may not even be made with bristles but rather with a rubber like foam inserted over a plastic stem that is longer and thicker than that attached to most bristled interdental brushes. These brushes may not be able to be used as desired in the designs of U.S. Pat. No. 5,201,091 to E. B. Tarrson et al., issued Apr. 13, 1993 entitled "Toothbrush". Thus, it is necessary to have an interdental brush holder that can accommodate brush stems of varying lengths. Therefore, it is desirable to have an interdental brush holder that is designed to accommodate various replacement tips.

Additionally, interdental brush holders having a sleeve/shaft arrangement, such as U.S. Pat. No. 4,030,199 to J. R. Russell, issued May 12, 1975, entitled "Handle For Disposable Appliance", and U.S. Pat. No 4,222,143 to E. B. Tarrson et al., issued Sep. 16, 1980 entitled "Interproximal Brush Handle", lock their interdental brush tip stems to the handle through unregulated frictional force. When the stem of an interdental brush tip is engaged as desired in such designs, users are unable to determine if the stem is over or under secured to the handle. If the stem is under secured it may come loose in a user's mouth. If it is overly secured, it may prevent the replacement of fresh tips, thereby rendering even a new brush handle useless. Thus, it is necessary for a sleeve-based interdental brush holder to have a defined, positive lock to allow a user to determine if a stem is properly secured to the handle. Therefore, it is desirable to have an interdental brush holder that not only has a defined positive lock but such a lock should signal to the user visibly and/or audibly that it has engaged and has accurately secured the stem of the interdental brush tip.

SUMMARY OF THE INVENTION

The present invention is directed to a support for an interdental toothcleaner of the type having an elongated, relatively stiff but bendable stem with cleaning means secured to the stem. The support includes an elongated neck having an end, and a hole extending transversely through the neck adjacent but spaced from the end. A groove extends longitudinally along the neck from the end. A cap is slidable longitudinally along the neck from the end. The cap has a first slot therein extending longitudinally along a portion thereover over the groove in the neck. The first slot is shorter than the length of the cap with the ends of the first slot being spaced from the ends of the cap. The hole in the stem is adapted to receive the stem of an interdental toothcleaner which also extends through the first slot in the cap. One end of the first slot is adapted to engage the stem as the cap is slid in one direction along the neck to bend the stem and press it into the groove in the neck, and thereby lock the toothbrush to the support. The other end of the first slot is adapted to engage the end of the stem when the cap is slid in the opposite direction along the neck to lift the stem out of the groove and thereby allow the toothcleaner to be removed from the support.

BRIEF DESCRIPTION OF THE DRAWINGS

FIG. 1 is a side view of one form of an interdental toothcleaner holder for the interdental toothcleaner support of the present invention;

FIGS. 2, 3 and 4 are bottom views of the end of the interdental toothcleaner support of the present invention in various steps of operation;

FIGS. 8 and 9 are sectional views of the end portion of the interdental toothcleaner support of the present invention showing the support being closed to secure an interdental toothcleaner in the support;

FIG. 10 is a sectional view similar to FIG. 8 and 9 showing the toothcleaner completely secured in the support;

FIG. 11 is a sectional view similar to FIG. 8 showing the support being opened to allow removal of the toothcleaner FIG. 12 is a side view of another form of the interdental toothcleaner support of the present invention.

DETAILED DESCRIPTION

Referring to FIG. 1, there is shown an interdental toothcleaner holder 10 on which is an interdental toothcleaner support 12 of the present invention. The toothcleaner holder 10 comprises a housing 14 containing a sonically resonating motor, not shown. Such a structure is shown and described in U.S. Pat. No. 5,123,841 (Millner), issued Jun. 23, 1992, which is incorporated herein by reference. The toothcleaner support 12 is removable mounted on the end of the housing 14 so that it can be vibrated by the motor within the housing 14.

Figure 5:
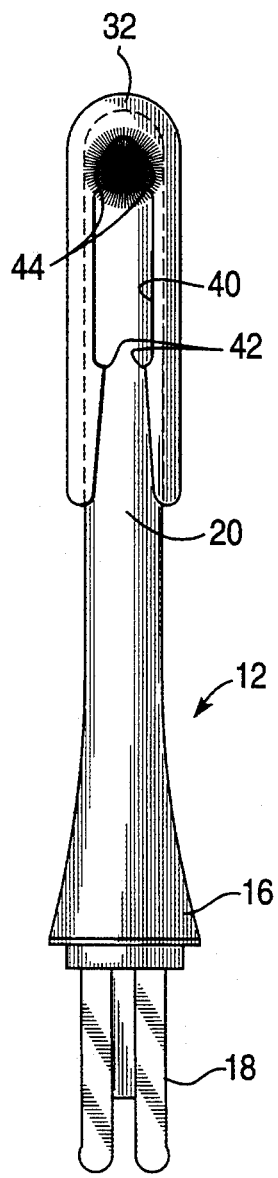
FIG. 5 is a bottom view of the interdental toothcleaner support of the present invention.
Figure 6:
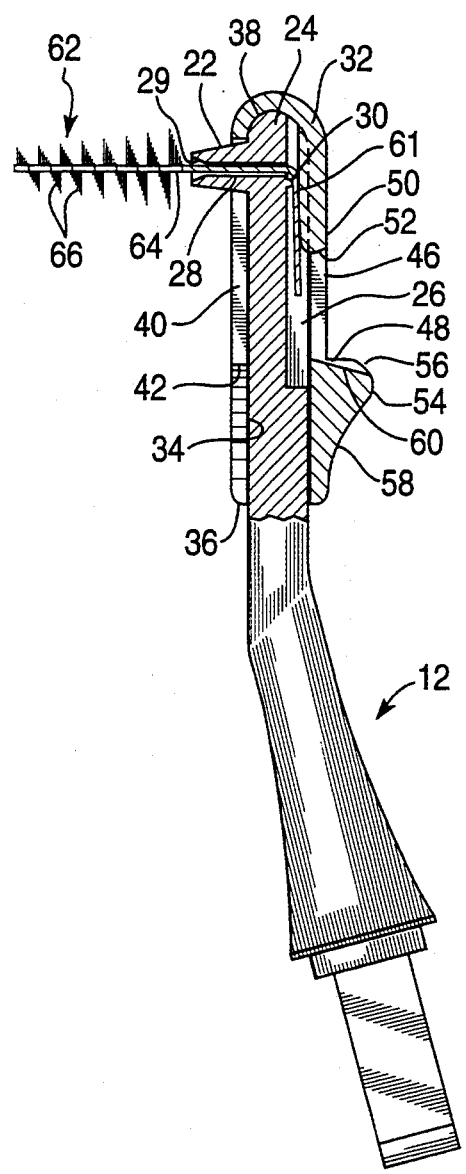
FIG. 6 is a side view, partially sectioned, of the interdental toothcleaner support shown in FIG. 5.
Figure 7:
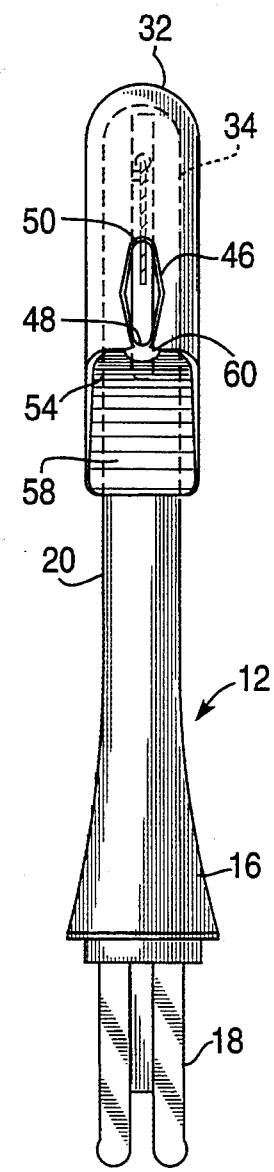
FIG. 7 is a top view of the interdental toothcleaner support shown in FIGS. 5 and 6.

As shown in FIGS. 5, 6 and 7, the toothcleaner support 12 is an elongated member made of a rigid material, such as a plastic. Support 12 has an enlarged circular base portion 16 at one end having prongs 18 projecting therefrom. The prongs 18 fit into openings in the end of the housing 14 to secure the support 12 on the housing 14. A neck 20 extends from the base portion 16 and is at an angle with respect to the base portion 16. The neck 20 is of a diameter much smaller than that of the base portion 16. A tip 22 projects radially from the front of the neck 20 adjacent the end 24 thereof. The tip 22 is in the form of a frustrated, triangular pyramid with its outer end being smaller than its end at the neck 20. A narrow groove 26 extends longitudinally along the neck 20 from the end 24 thereof. The groove 26 is along the back of the neck 20 diametrically opposite the tip 22. A hole 28 extends through the tip 22 and diametrically across the neck 20 to the groove 26. The outer end 29 of the hole 28 in the tip 22 flares outwardly to allow for ease of inserting the stem of a toothcleaner in the hole 28. A bump 30 projects from the bottom of the groove 26 on the side of the hole 28 away from the end 24 of the neck 20.

A cap 32 slidably fits over the end of the neck 20. The cap 32 has a passage 34 therethrough which is of a diameter slightly larger than that of the neck 20 so that the neck 20 can slide within the passage 34. The passage 34 is open at the back end 36 of the cap 32 but is closed at the front end 38 of the cap 32. A slot 40 extends through the cap 32 to the passage 34 along the front side of the cap 32. The slot 40 extends from the open end of the passage 34 to just short of the closed end of the passage 34. At the open end of the passage 34, the slot 40 is slightly wider that the width of the tip 22 on the neck 20, and tapers downwardly in width to a first detent 42 where the slot 40 is slightly narrower than the width of the tip 22. The slot 40 then has a width substantially the same as the tip 22 until a second detent 44 adjacent, but spaced from the closed end of the passage 34. The second detent 44 makes the slot 40 narrower than the width of the tip 22. Between the second detent 44 and the closed end of the passage 34, the slot 40 is of a size substantially equal to the size of the tip 22. As shown in FIG. 2, when the cap 32 is slid onto the end of the neck 20, the tip 22 passes into and along the slot 40 until it contacts the first detent 42. By pressing firmly against the cap 32, the first detent 42 can be spread apart sufficiently to allow the tip 22 to pass therethrough. The detent 42 then springs back to prevent the tip 22 from sliding out of the slot 40. As shown in FIG. 3, the cap 32 can then be slid back and forth along the neck 20 with the tip 22 passing along the slot 40 between the first and second detents 42 and 44. As shown in FIG. 4, the cap 32 can be pressed firmly inwardly to move the tip 22 past the second detent 44 into the end portion of the slot 40 beyond the second detent 44. The second detent 44 holds the tip 22 in the +end portion of the slot 40 until the cap 32 is pushed firmly away from the neck 20.

As shown in FIGS. 6 and 7, a second slot 46 extends through the back of the cap 32 diametrically opposite the slot 40. The second slot 46 is closed at both ends and is much shorter than the slot 40. The back end 48 of the second slot 46 is diametrically opposite the first detent 42, but the front end 50 of the second slot 46 is spaced from the second detent 44. The end surface 52 of the second slot 46 at its front end 50 ramps backwardly from the surface of the cap 32 toward the passage 34 and then curves forwardly to the passage 34. A projection 54 extends outwardly from the cap 32 at the back end 48 of the second slot 46. The projection 54 has a front surface 56 which extends substantially radially outwardly from the cap 32, and a curved back surface 58 against which a finger can be pressed to move the cap 32 along the neck 20. The front surface 56 of the projection 54 has a narrow groove 60 extending therealong. The groove 60 extends along the back end 48 of the second slot 46 to the passage 34 in the cap 32. The cap 32 has a key 61 projecting radially inwardly from its inner surface into the groove 26 in the neck 20. This prevents rotation of the cap 32 around the neck 20 but allows the cap 32 to move longitudinally along the neck 20.

In the use of the toothcleaner holder 10 to hold an interdental toothcleaner, such as an interdental toothbrush 62, the cap 32 is slid onto the end of the neck 20 with the tip 22 fitting into the slot 40. The cap 32 is pushed along the neck 20 until the tip 22 is snapped past the first detent 42. The cap 32 can then be slid back and forth along the neck 20 between the first and second detents 42 and 44. The interdental toothbrush 62 is of the type shown and described in U.S. Pat. No. 5,123,841 to D. E. Millner and comprises a twisted wire stem 64 having bristles 66 extending and clamped between the wires of the stem 64 and extending radially therefrom. The bristles 66 are arranged partially along the stem 64 from one end of the stem 64 leaving the other end of the stem 64 free.

As can be seen from FIG. 8, with the cap 32 being positioned just beyond the first detent 42, the back end 48 of the second slot 46 is directly opposed the tip 22. The free end of the stem 64 of the toothbrush 62 is inserted into and through the hole 28 in the tip 22 until the free end of the stem 64 projects through and beyond the second slot 46. The cap 32 is then slid back along the neck 20 until the front end 50 of the second slot 46 reaches the stem 64. As shown in FIG. 9, further movement of the cap 32 back along the neck 20 causes the ramped back surface 52 to engage the stem 64 and press the stem 64 backwardly. This causes the stem 64 to bend across the bump 30 on the bottom of the groove 26. As shown in FIG. 10, as the cap 32 moves further backwardly, the ramped back surface 52 presses the bent end of the stem 64 downwardly into the groove 26 in the neck 20 and the cap 32 extends over the bent end of the stem 64 to secure the stem 64 into the groove 26. This secures the stem 64 to the neck 20 and the toothbrush 62 to the support 12. When the cap 32 is moved backwardly until the tip 22 reaches the second detent 44, the cap 32 is pushed firmly further until the tip 22 pushes pass the second detent 44 into the front end portion of the slot 40. This holds the cap 32 on the neck 20 with the cap 32 securing the toothbrush 62 to the support 12. The second detent 44 prevents accidental movement of the cap 32 during use of the toothbrush 62.

When the toothbrush 62 becomes worn or it is otherwise desired to replace the toothbrush 62, the cap 32 is pushed forwardly on the neck 20 until the tip 22 snaps past the second detent 44 and enters the main central portion of the slot 40. As shown in FIG. 11, as the cap 32 is moved from over the bent end of the stem 64 of the toothbrush 62, the inherent resiliency of the metal stem 64 causes the stem 64 to lift slightly upwardly out of the groove 26 so that the end of the stem 64 is out of the groove 26. Further moving the cap 32 forwardly on the neck 20 causes the back surface 48 of the second slot 46 to engage the end of the stem 64 and cause it to slide upwardly in the groove 60 in the back surface 48 and the projection 54. Thus, as the cap 32 is moved forwardly on the neck 20, the stem 64 of the toothbrush 62 is pushed upwardly in the groove 60. When the tip 22 reaches the first detent 42, the stem 64 is substantially straight so that the toothbrush 62 can be pulled from the hole 28 and removed from the support 12. The stem 64 of a new toothbrush 62 can then be inserted in the hole 28 and secured to the support 12 in the manner described above. In securing or removing a toothbrush 62 from the support 12, the cap 32 can be slid back and forth along the neck 20 by pressing a finger against the surface 58 of the projection 54 on the cap 32.

Referring to FIG. 12, another form of the interdental toothbrush holder of the present invention is generally designated as 68. Toothbrush holder 68 comprises a handle 70 having a toothbrush support 12 extending from and integral with one end thereof. The toothbrush support 12 is identical in structure to the support shown in FIGS. 8–11 previously described. The handle 70 may be hollow and have a removable cap at its free end. This allows extra toothbrushes 62 to be stored within the handle 70. The toothbrush holder 68 operates in the same manner as the toothbrush holder 10 except that it is operated manually rather than being sonically actuated.

Thus there is provided by the present invention an interdental toothcleaner support for a toothcleaner holder which allows for ease of removing and replacing the interdental toothcleaners, such as interdental toothbrushes and the like. However, the toothcleaner holder firmly holds the toothcleaner without over tightening and with a positive lock, and prevents accidental release of the toothcleaner even when the holder is being moved about, either manually or sonically energized, during use. Also, the toothcleaner holder of the present invention is relatively simple in construction and formed of only a few parts so as to be inexpensive to manufacture, but is able to sustain moderate abuse. Although the toothcleaner has been shown and described as a toothbrush having bristles projecting from a metal stem, the toothcleaner holder of the present invention can be used with other types of interdental toothcleaners. For example, the toothcleaner can have a plastic stem instead of a metal stem, and/or can have a plastic sponge type cleaner on the stem instead of bristles.

What is claimed is:

1. A support for an interdental toothcleaner which toothcleaner has a relatively stiff but bendable stem and cleaning means on the stem, said support comprising:

an elongated neck having an end;

a tip projecting radially from the neck adjacent to but spaced from the end thereof;

a hole extending transversely through the tip and the neck;

a groove in said neck extending longitudinally along said neck from said end and crossing said hole diametrically opposite the tip;

a cap having a passage therethrough through which the neck extends so that the cap is slidable longitudinally along said neck from said end, said passage having a closed end and an open end;

a first slot in the cap extending longitudinally along a portion of the cap over the groove in the neck, said first slot being shorter than the length of the cap with the ends of the first slot being spaced from the ends of the cap; and a second slot extending through and longitudinally along the cap through which the tip extends to allow the cap to be moved, said second slot extending from the open end of the cap to a point adjacent but spaced from the closed end of the cap;

the hole in the neck adapted to receive the stem of an interdental toothcleaner which also extends through the first slot in the cap, means at one end of the first slot to engage said stem as the cap is slid in one direction along the neck to bend the stem and press it into the groove in the neck and thereby lock the toothcleaner to the support, and means at the other end of the first slot to engage the end of the stem which the cap is slid in the opposite direction along the neck to lift the stem out of the groove and thereby allow the toothcleaner to be removed from the support.

2. The support of claim 1 in which the hole through the tip flares outwardly at the end of the tip to provide for ease of inserting the stem of the toothcleaner into the hole.

3. The support of claim 1 including a key extending radially inwardly from the surface of the passage in the cap and fitting into the groove in the neck to prevent rotation of the cap on the neck but allow longitudinal movement of the cap on the neck.

4. The support of claim 1 in which the second slot has a first set of detents adjacent but spaced from the open end thereof which detents reduce the width of the second slot so as to limit the movement of the cap on the neck in one direction.

5. The support of claim which the second slot has a second set of detents adjacent but spaced from the closed end of the second slot which second set of detents reduces the width of the second slot so as to limit movement of the cap on the neck in the opposite direction.

6. The support of claim 5 in which the second set of detents is spaced from the closed end of the second slot a distance substantially equal to the cross-sectional dimension of the tip so that when the cap is moved sufficiently to place the tip in the space between the closed end of the second slot and the second set of detents the cap will be held in that position.

7. The support of claim 6 further comprising a projection extending outwardly from the cap at an end of the first slot, said projection adapted to be engaged by a users finger to move the cap along the neck.

8. The support of claim 7 in which the projection is at the end of the first slot adjacent the open end of the cap.

9. The support of claim 8 in which the projection has a surface at the end of the first slot and a narrow groove extends along the said surface of the projection and the end surface of the first slot, said groove being of a width corresponding to the diameter of the stem of a toothcleaner.

10. The support of claim 9 in which the end surface of the first slot which is adjacent the closed end of the cap is curved.

11. The support of claim 10 including a bump projection from the bottom of the groove in the neck adjacent the hole through the neck, said bump being on the side of the hole away from the end of the neck.

12. The support of claim 1 in which the neck has means at one end for mounting the support on a handle having means for sonically energizing the support.

13. The support of claim 1 in which the neck extends from and is integral with a handle.

14. A support for an interdental toothcleaner which toothcleaner has a relatively stiff but bendable stem and cleaning means on the stem, said support comprising:
 an elongated neck having an end;
 a tip projecting radially from the neck adjacent to but spaced form the end of the neck;
 a hole extending through the tip and transversely through the neck;
 a groove in said neck extending longitudinally along said neck from said end diametrically opposite the tip and crossing the hole;
 a cap slidable longitudinally along said neck from said end;
 a first slot extending through and longitudinally along a portion of the cap over the groove in the neck, said first slot being shorter than the length of the cap with the ends of the first slot being spaced from the end of the cap; and
 a second slot extending through and longitudinally along the cap from one end of the cap but spaced from the other end of the cap so that the second slot has one open end and one closed end with the tip extending through the second slot to allow the cap to be moved longitudinally along the neck;
 the hole in the neck adapted to receive the stem of an interdental toothcleaner which also extends through the first slot in the cap, one end of the first slot being adapted to engage said stem as the cap is moved in one direction along the neck to bend the stem and press it into the groove in the neck and thereby lock the toothcleaner to the support.

15. The support of claim 14 in which the second slot has a first set of detents adjacent but spaced from the open end thereof which detents reduce the width of the second slot so as to limit the movement of the cap on the neck in one direction.

16. The support of claim 15 in which the second slot has a second set of detents adjacent but spaced from the closed end of the second slot which second set of detents reduces the width of the second slot so as to limit movement of the cap on the neck in the opposite direction, the second set of detents being spaced from the closed end of the second slot a distance substantially equal to the cross-sectional dimension of the tip so that when the cap is moved sufficiently to place the tip in the space between the closed end of the second slot and the second set of detents, the cap will be held in that position.

17. The support of claim 14 including means at the other end of the first slot for engaging the end of the stem of the toothcleaner when the cap is slid in the opposite direction along the neck to lift the stem out of the groove and thereby allow the toothcleaner to be removed from the support.

* * * * *